US010048026B2

(12) United States Patent
Yoshida et al.

(10) Patent No.: US 10,048,026 B2
(45) Date of Patent: Aug. 14, 2018

(54) ANTIFOULING COATING, HEAT EXCHANGER PROVIDED WITH SAME, AND METHOD FOR MANUFACTURING HEAT EXCHANGER

(71) Applicant: MITSUBISHI ELECTRIC CORPORATION, Chiyoda-ku (JP)

(72) Inventors: Yasuhiro Yoshida, Chiyoda-ku (JP); Yoshinori Yamamoto, Chiyoda-ku (JP); Osamu Hiroi, Chiyoda-ku (JP)

(73) Assignee: MITSUBISHI ELECTRIC CORPORATION, Chiyoda-ku (JP)

( * ) Notice: Subject to any disclaimer, the term of this patent is extended or adjusted under 35 U.S.C. 154(b) by 596 days.

(21) Appl. No.: 14/424,788

(22) PCT Filed: Aug. 22, 2013

(86) PCT No.: PCT/JP2013/072382
§ 371 (c)(1),
(2) Date: Feb. 27, 2015

(87) PCT Pub. No.: WO2014/034514
PCT Pub. Date: Mar. 6, 2014

(65) Prior Publication Data
US 2015/0241146 A1  Aug. 27, 2015

(30) Foreign Application Priority Data

Sep. 3, 2012 (JP) .................... 2012-193238

(51) Int. Cl.
*F28F 19/06* (2006.01)
*C09D 1/00* (2006.01)
(Continued)

(52) U.S. Cl.
CPC .............. *F28F 19/06* (2013.01); *A01N 59/16* (2013.01); *B23P 15/26* (2013.01); *C09D 1/00* (2013.01);
(Continued)

(58) Field of Classification Search
CPC .... F28F 2245/02; F28F 2245/04; F28F 19/06; B23P 15/26; C09D 5/1662; C09D 5/1618; A01N 59/16
See application file for complete search history.

(56) References Cited

U.S. PATENT DOCUMENTS 5,069,816 A * 12/1991 DeSantis ............... C01B 33/159
502/236
6,716,513 B1 * 4/2004 Hasuo ................... C03C 17/007
428/141
(Continued)

FOREIGN PATENT DOCUMENTS

EP     1 970 196 A2     9/2008
EP     1 970 196 A3     9/2008
(Continued)

OTHER PUBLICATIONS

International Search Report dated Nov. 19, 2013 in PCT/JP13/072382 filed Aug. 22, 2013.
Extended European Search Report dated Apr. 11, 2016 in Patent Application No. 13833583.1.

*Primary Examiner* — Tho V Duong
(74) *Attorney, Agent, or Firm* — Oblon, McClelland, Maier & Neustadt, L.L.P.

(57) ABSTRACT

The present invention provides an antifouling coating formed from a water-based coating composition comprising 0.1% by mass to 10% by mass of ultrafine silica particles having an average particle size equal to or less than 25 nm, 5% by mass to 50% by mass, relative to the ultrafine silica particles, of a zirconium compound which is at least one
(Continued)

selected from zirconium chloride and zirconyl chloride, and 30% by mass to 99.5% by mass of water. In accordance with the present invention, it is possible to provide an antifouling coating that can maintain the antifouling performance and hydrophilicity and prevent corrosion of fins even under an environment with a large amount of contaminating substances, such as metal particles, in the air.

13 Claims, 4 Drawing Sheets

(51) Int. Cl.
*F28F 19/02* (2006.01)
*C09D 5/16* (2006.01)
*A01N 59/16* (2006.01)
*B23P 15/26* (2006.01)
*C09D 7/40* (2018.01)
*C09D 7/61* (2018.01)
*C08K 3/16* (2006.01)
*C08K 3/36* (2006.01)

(52) U.S. Cl.
CPC ......... *C09D 5/1612* (2013.01); *C09D 5/1618* (2013.01); *C09D 5/1662* (2013.01); *C09D 5/1687* (2013.01); *C09D 7/40* (2018.01); *C09D 7/61* (2018.01); *C09D 7/67* (2018.01); *F28F 19/02* (2013.01); *C08K 3/16* (2013.01); *C08K 3/36* (2013.01); *F28F 2245/02* (2013.01); *Y10T 29/49378* (2015.01)

(56) References Cited

U.S. PATENT DOCUMENTS

| | | | |
|---|---|---|---|
| 8,801,850 B2 | 8/2014 | Yoshida et al. | |
| 8,906,298 B2* | 12/2014 | Koike | B32B 7/02 |
| | | | 422/1 |
| 2008/0226928 A1 | 9/2008 | Tanaka et al. | |
| 2010/0096114 A1 | 4/2010 | Yoshida et al. | |
| 2010/0233374 A1 | 9/2010 | Kawakami | |
| 2011/0259571 A1* | 10/2011 | Yamasaki | C09D 5/14 |
| | | | 165/185 |

FOREIGN PATENT DOCUMENTS

| | | |
|---|---|---|
| EP | 2 105 470 A2 | 9/2009 |
| EP | 2 105 470 A3 | 9/2009 |
| EP | 2 112 207 A1 | 10/2009 |
| EP | 2 119 996 A1 | 11/2009 |
| EP | 2 413 085 A1 | 2/2012 |
| JP | 55 62971 | 5/1980 |
| JP | 8 261688 | 10/1996 |
| JP | 10 36757 | 2/1998 |
| JP | 11 201688 | 7/1999 |
| JP | 2000 309068 | 11/2000 |
| JP | 2001 40294 | 2/2001 |
| JP | 2002 241963 | 8/2002 |
| JP | 2008 253985 | 10/2008 |
| JP | 2009 229040 | 10/2009 |
| JP | 2010 65148 | 3/2010 |
| JP | 2010 96416 | 4/2010 |
| JP | 2010 235436 | 10/2010 |
| JP | 2012 189272 | 10/2012 |
| WO | 2008 087877 | 7/2008 |

* cited by examiner

PRIOR ART

ANTIFOULING COATING, HEAT EXCHANGER PROVIDED WITH SAME, AND METHOD FOR MANUFACTURING HEAT EXCHANGER

TECHNICAL FIELD

The present invention relates to an antifouling coating that can prevent adhesion of contamination to a surface, and to a heat exchanger provided with the coating. More particularly, the present invention relates to an antifouling coating for use in metal processing (welding, cutting, etc.) sites, enterprises where metal dust is handled, vehicles such as railway vehicles, and related facilities, and also to heat exchangers for air conditioners.

BACKGROUND ART

Surfaces of various products can look dirty, cause sanitary problems, or demonstrate performance degradation caused by corrosion or the like, due to exposure to various contaminating substances from the environment. Among such products, heat exchangers in air conditioning equipment are highly susceptible to contamination from the environment due to the functions thereof, and the contamination easily causes a variety of failures.

A heat exchanger has a structure in which a large number of fins (for example, aluminum fins) are attached to a pipe in which a coolant flows, and heat exchange efficiency is increased by fins with a large surface area. Condensed water can easily adhere to the fin surface during cooling and warming, and the ventilation resistance can increase and heat exchange efficiency can decrease due to a phenomenon of the fins being connected to each other by the condensed water (referred to hereinbelow as "bridge phenomenon"). In particular, since the bridge phenomenon is easily induced by contamination such as dust adhering to the fin surface, the bridge phenomenon is typically prevented by forming an organic or inorganic hydrophilic coating that excels in antifouling performance on the fin surface. In the present description, the "antifouling performance" means the performance such that contamination is unlikely to adhere and the adhered contamination is easily removed.

However, when an inorganic hydrophilic coating contains a large amount of an inorganic component such as water glass or boehmite, the coating easily adsorbs odor. For this reason, organic hydrophilic coatings are often used. Meanwhile, organic components of organic hydrophilic coatings are easily decomposed, degraded, or dissolved in condensed water with the passage of time, and the antifouling performance or hydrophilicity of the hydrophilic coating are degraded.

Accordingly, techniques for forming hydrophilic coatings by using various coating materials have been suggested for preventing the degradation of antifouling performance and hydrophilicity of hydrophilic coatings. For example, Patent Document 1 suggests a method for forming a hydrophilic coating by using a coating material comprising a modified polyvinyl alcohol and a crosslinking agent. Patent Document 2 suggests a method for forming a hydrophilic coating by using a coating material comprising carboxymethyl cellulose, polyethylene glycol, and a crosslinking agent. Patent Document 3 suggests a technique for forming a thin film constituted by ultrafine silica particles and fluororesin particles. By using a configuration in which hydrophobic portions are present in a spot-like manner on a hydrophilic surface, it is possible to prevent the adhesion of hydrophilic or hydrophobic contaminants of various properties, while maintaining high hydrophilicity of the entire film. Since the film is thin, the problem of odor adsorption can be avoided and the film can be adapted to a heat exchanger.

PRIOR ART REFERENCES

Patent Documents

Patent Document 1: Japanese Patent Application laid-open No. 10-36757
Patent Document 2: Japanese Patent Application laid-open No. 8-261688
Patent Document 3: WO 2008/087877

SUMMARY OF INVENTION

Technical Problem

The antifouling performance and hydrophilicity of an antifouling coating are typically degraded by exposure to water, heat, sunlight, and air, and the degradation of coating can result in metal corrosion or resin degradation in the fin on which the coating is provided. In particular, when a contaminating substance includes a large amount of metal particles of iron, copper, or alloys thereof, more particularly an iron powder, it can easily cause the degradation of antifouling performance and hydrophilicity of the hydrophilic coating and corrosion of fin. Patent Documents 1, 2, and 3 do not resolve the problem relating to degradation of antifouling performance and hydrophilicity of hydrophilic coating and corrosion of fin which is caused by adhesion of such contaminating substances.

Thus, the hydrophilic coatings described in Patent Documents 1, 2, and 3 can maintain the antifouling performance and hydrophilicity under the usual environment with a small amount of contaminating substances, such as metal particles, in the air, but the antifouling performance and hydrophilicity gradually degrade due to the adhesion of the contaminating substances under an environment with a large amount of contaminating substances such as metal particles (for example, in metal processing (welding, cutting, etc.) sites, enterprises where metal dust is handled, vehicles such as railway vehicles, and related facilities). More specifically, since the hydrophilic coatings described in Patent Documents 1 and 2 are organic coatings, metal ion components created by dissolution of the contaminating substances in condensed water act as a catalyst and enhance the degradation of organic components. As a result, the antifouling performance and hydrophilicity of the hydrophilic coatings are degraded and fins are corroded. In Patent Document 3, as a result of corrosion of even a very small number of metal particles adhered to the thin film, metal ions that have permeated through the film degrade the base material, or the antifouling performance and hydrophilicity can be degraded by corroded iron particles firmly bonded to the surface of ultrafine silica particles.

The present invention has been created to resolve the above-described problems, and it is an objective thereof to provide an antifouling coating that can maintain the antifouling performance and hydrophilicity and prevent corrosion of fins even under an environment with a large amount of contaminating substances, such as metal particles, in the air, and also provide a heat exchanger having such a coating, and a manufacturing method therefor.

Solution to the Problem

The inventors have conducted a comprehensive study with the object of resolving the above-described problem, and the results obtained demonstrate that an antifouling coating formed from a water-based coating composition comprising ultrafine silica particles having a specific average particle size and a zirconium compound which is at least one selected from zirconium chloride and zirconyl chloride at a specific ratio can maintain the antifouling performance and hydrophilicity even under an environment with a large amount of contaminating substances such as metal particles. This finding led to the creation of the present invention.

Thus, the present invention provides an antifouling coating formed from a water-based coating composition comprising 0.1% by mass to 10% by mass of ultrafine silica particles having an average particle size equal to or less than 15 nm, 5% by mass to 50% by mass, relative to the ultrafine silica particles, of a zirconium compound which is at least one selected from zirconium chloride and zirconyl chloride, and 30% by mass to 99.5% by mass of water.

The present invention also provides a heat exchanger comprising a pipe in which a coolant flows, and a fin attached to the pipe, the heat exchanger comprising a hydrophilic organic coating formed on the fin, a reaction layer obtained by reacting a zirconium compound which is at least one selected from zirconium chloride and zirconyl chloride on a surface layer of the hydrophilic organic coating, and an inorganic coating provided on the reaction layer and formed from a water-based coating composition comprising 0.1% by mass to 10% by mass of ultrafine silica particles having an average particle size equal to or less than 15 nm.

The present invention also provides a heat exchanger comprising a pipe in which a coolant flows, and a fin attached to the pipe, the heat exchanger comprising a hydrophilic organic coating formed on the fin, and an inorganic coating provided on the hydrophilic organic coating and formed from a water-based coating composition comprising 0.1% by mass to 10% by mass of ultrafine silica particles having an average particle size equal to or less than 15 nm, 5% by mass to 50% by mass, relative to the ultrafine silica particles, of a zirconium compound which is at least one selected from zirconium chloride and zirconyl chloride, and 30% by mass to 99.5% by mass of water.

Advantageous Effects of the Invention

In accordance with the present invention, it is possible to form an antifouling coating which has high hydrophilicity and antifouling ability and resists to adhesion of contaminants and degradation even in the presence of metal particles or the like. Further, in a heat exchanger provided with a fin with the antifouling coating formed thereon, antifouling performance and hydrophilicity can be maintained and the fin can be prevented from corrosion even under an environment with a large amount of contaminating substances, such as metal particles, in the air.

DESCRIPTION OF EMBODIMENTS

Embodiment 1

At metal processing (welding, cutting, etc.) sites, enterprises where metal dust is handled, vehicles such as railway vehicles, and related facilities, metal particles such as particles of iron, copper, zinc, or alloys thereof, and particles to which such metal particles have adhered float in the air (such particles will be together referred to hereinbelow as "metal particles"). A coating constituted by an inorganic material, an organic material, or a combination thereof, in particular highly hydrophilic coating having a large number of polar groups, such as hydroxyl groups, on the surface, is degraded by adhesion of the metal particles, or the metal particles are easily firmly attached thereto.

Figure 1:
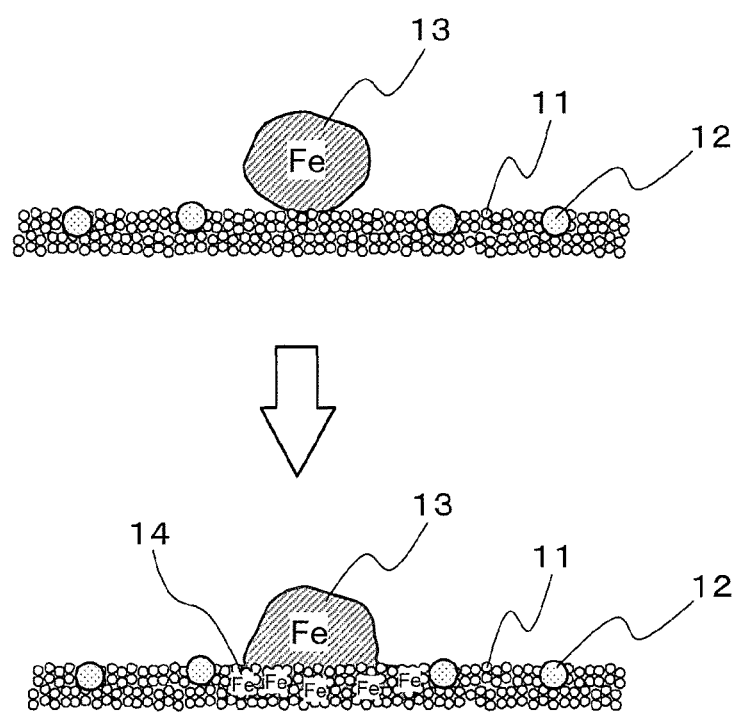
FIG. 1 is a schematic diagram illustrating the degradation of the conventional coating caused by adhesion of metal particles.

FIG. 1 is a schematic diagram illustrating the degradation of the conventional coating caused by adhesion of metal particles. In the conventional coating depicted in FIG. 1, ultrafine silica particles 11 serving as fine inorganic particles are aggregated and fluororesin particles 12 are present in a spot-like fashion. With the coating of such a configuration, dust is unlikely to adhere, as will be described hereinbelow, but when the coating is wetted with water, a metal particle 13 (for example, an iron particle) adheres thereto. The metal particle 13 is partially corroded by water, thereby forming metal ions 14 adsorbed by the ultrafine silica particles 11 in the coating. Under such conditions, the metal particle 13 is strongly attached to the coating, the coating is stained, and the antifouling ability is degraded by the attached metal particles 13.

Figure 2:
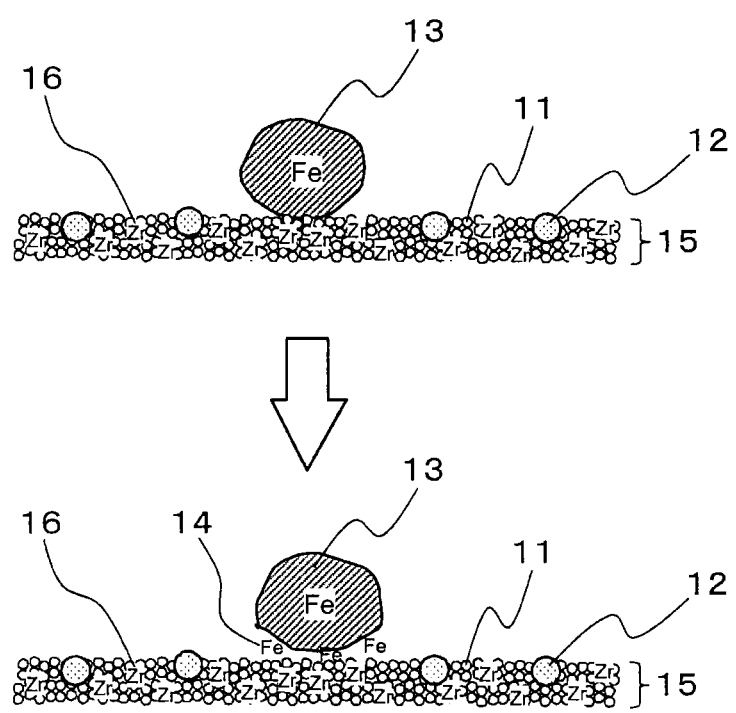
FIG. 2 is a schematic diagram demonstrating that the antifouling coating according to Embodiment 1 of the present invention is unlikely to be degraded by the adhesion of metal particles.

Meanwhile, the water-based coating composition for obtaining the antifouling coating according to Embodiment 1 of the present invention comprises ultrafine silica particles 11, a zirconium compound which is at least one selected from zirconium chloride and zirconyl chloride, and water. As a result of coating the water-based coating composition on an article surface and drying, it is possible to form an antifouling coating that can demonstrate high durability and antifouling ability with respect to the attachment of metal particles which is caused by corrosion and reaction induced by the metal ions 14 and can demonstrate good hydrophilicity and antifouling ability even under an environment in which the metal particle 13 can easily adhere. FIG. 2 is a schematic diagram demonstrating that the antifouling coating 15 according to Embodiment 1 is unlikely to be degraded by the adhesion of the metal particle 13. In FIG. 2, a Zr atom 16 introduced by zirconium chloride or zirconyl chloride forms a bond with a hydroxyl group, or the like, on the surface of the ultrafine silica particles 11, thereby protecting the surface of the antifouling coating 15. As a result of the introduced Zr atom 16 acting as a protective group of the hydroxyl group present on the surface of the antifouling coating 15, it is apparently possible to inhibit the adsorption of the metal ions 14, such as an iron ions generated from the metal particle 13, and the attachment of the metal particle 13. FIG. 2 illustrates a state in which the hydrophobic fluororesin particles 12 are present in a spot-like fashion in the thin hydrophilic silica film, but the fluororesin particles 12 further inhibit the adhesion of dust, and even when such particles are not present, the effect of inhibiting the attachment of the metal particle 13 can be obtained as a result of adding zirconium chloride or zirconyl chloride. Thus, since the surface of such antifouling coating 15 is constituted by a continuous hydrophilic portion in which hydrophobic portions are present, when water droplets adhere thereto, the droplets are easily spread and the film, when viewed as a whole, demonstrates high hydrophilicity. Further, because of a configuration in which hydrophilic portions and hydrophobic portions are finely mixed, even when hydrophilic dust or hydrophobic dust attempts to adhere, the dust comes into contact with the surface having an opposite nature and cannot stably adhere to the surface. Thus, a strong antifouling ability is demonstrated with respect to a wide range of dust-like contaminants.

There are various types of organometallic compounds acting similarly to zirconium chloride and zirconyl chloride, examples thereof including alkoxides or chelates other than chlorides, and compounds of metals other than zirconium, such as titanium and aluminum. However, by contrast with those compounds, where zirconium chloride and zirconyl chloride are added to a water-based coating composition comprising water as the main component, they can be stably present therein as zirconium hydroxide (zirconium chloride becomes zirconyl chloride in an aqueous solution), high reactivity can be demonstrated when the coating is formed, and the effect of the metal particle 13 can be efficiently suppressed. Further, where a zirconium compound which is at least one selected from zirconium chloride and zirconyl chloride is added to a water-based coating compound, although hydrochloric acid, or the like, is produced as a byproduct, it is unlikely to remain in the antifouling coating 15 or, even when the byproduct remains, it produces little effect on antifouling ability. Another merit of zirconium chloride and zirconyl chloride is that it is very safe for humans. When other organometallic compounds are added, various byproducts derived from chelates or alkoxides can be generated and can adversely affect the antifouling performance.

The amount of the zirconium compound which is at least one selected from zirconium chloride and zirconyl chloride is 5% by mass or more to 50% by mass or less, preferably 10% by mass or more to 40% by mass or less on the basis of the solid weight of the ultrafine silica particles. Where the content of the zirconium compound is less than 5% by mass, the effect of the metal particle 13 cannot be sufficiently suppressed. Meanwhile, it is undesirable that the content of the zirconium compound be above 50% by mass because the pores in the porous silica film formed by cohesion of the ultrafine silica particles 11 are filled by the zirconium compound and, therefore, the antifouling coating 15 becomes too dense and the antifouling performance is degraded. The content of the zirconium compound, as referred to herein, is calculated on the basis of the mass of zirconium oxide when the entire zirconium in the added zirconium compound becomes zirconium oxide ($ZrO_2$).

Colloidal silica and fumed silica can be used as the ultrafine silica particles 11 in accordance with the present invention. The average particle size of the ultrafine silica particles 11 may be equal to or less than 25 nm, preferably 3 nm or more to 25 nm or less, more preferably 5 nm or more to 15 nm or less. The "average particle size" of the ultrafine silica particles 11 in the present description means the value of the number-average particle size of the ultrafine silica particles 11 measured by a particle size distribution meter of a laser beam scattering system or dynamic optical scattering system. Where the average particle size of the ultrafine silica particles 11 is too small, the particles are sometimes difficult to disperse uniformly in the water-based coating composition. Further, the dust adhesion inhibition effect demonstrated by the antifouling coating 15 is sometimes difficult to obtain. Meanwhile, where the average particle size of the ultrafine silica particles 11 exceeds 25 nm, the strength of the film of the antifouling coating 15 decreases and durability suitable for practical use sometimes cannot be obtained. The dust adhesion inhibition effect demonstrated by the antifouling coating 15 is obtained because the antifouling coating 15 is a porous silica film formed by cohesion of the ultrafine silica particles 11. This result can be explained as follows. As a result of the antifouling coating 15 being a porous silica film, even when dust collides with the surface, the contact surface area thereof is extremely small, and since the film density is low, an intermolecular force acting between the dust and the film is small. Where the condition of the average particle size being equal to or less than 25 nm is fulfilled, the ultrafine silica particles 11 may contain a certain amount of particles with an average size above 25 nm. For example, by using the ultrafine silica particles 11 with a twin-peak particle size distribution having particle size distribution peaks within a range from 5 nm or more to 15 nm or less and a range from 30 nm or more to 120 nm or less, it is possible to increase adequately the depressions and protrusions on the surface of the antifouling coating and improve the antifouling ability.

When a water-based coating composition is prepared, it is preferred that a dispersion of the ultrafine silica particles 11 that has a pH equal to or less than 4 be used in order to prevent cohesion when the zirconium compound which is at least one selected from zirconium chloride and zirconyl chloride is added. Further, in order to facilitate the formation of the antifouling coating 15, a typical binder such as a silicate, for example, sodium silicate and lithium silicate, a metal alkylate, a phosphoric acid amine, and ρ-alumina be used together with the ultrafine silica particles 11.

The content of the ultrafine silica particles 11 may be 0.1% by mass or more to 10% by mass or less, preferably 0.2% by mass or more to 10% by mass or less, more preferably 0.2% by mass or more to 4% by mass or less with respect to the water-based coating composition. Where the content of the ultrafine silica particles 11 is less than 0.1% by mass, the thickness of the antifouling coating 15 is too small and a sufficient hydrophilicity and dust adhesion inhibiting effect cannot be obtained. Where the content of the ultrafine silica particles 11 is above 10% by mass, protrusions and depressions on the surface of the antifouling coating 15 formed become large, dust is easily caught thereon, and antifouling ability is degraded.

The type of the fluororesin particles 12 is not particularly limited and suitable particles can be formed, for example, from PTFE (polytetrafluoroethylene), FEP (tetrafluoroethylene-hexafluoropropylene copolymer), PFA (tetrafluoroethylene-perfluoroalkyl vinyl ether copolymer), ETFE (ethylene-tetrafluoroethylene copolymer), ECTFE (ethylene-chlorotrifluoroethylene copolymer), PVDF (polyvinylidene fluoride), PCTFE (polychlorotrifluoroethylene), PVF (polyvinyl fluoride), fluoroethylene-vinyl ether copolymer, fluoroethylene-vinyl ester copolymer, copolymers and mixtures thereof, and compositions obtained by mixing other resins with those fluororesins. The average particle size of the fluororesin particles 12 is preferably 50 nm or more to 500 nm or less, more preferably 70 nm or more to 350 nm or less, most preferably 90 nm or more to 300 nm or less. The "average particle size" of the fluororesin particles 12 in the present description means the value of the number-average particle size of primary particles of the fluororesin particles 12 measured by a particle size distribution meter of a laser beam scattering system or dynamic optical scattering system. Where the average particle size of the fluororesin particles 12 is less than 50 nm, the effect demonstrated by the addition of the fluororesin sometimes cannot be demonstrated. Meanwhile, where the average particle size of the fluororesin particles 12 is above 500 nm, the protrusions and depressions on the surface of the antifouling coating 15 become too large and the antifouling effect can be lost.

When the fluororesin particles 12 are included in the water-based coating composition, the content thereof, as a mass ratio of the ultrafine silica particles 11 and the fluororesin particles 12, is preferably 70:30 to 95:5, more preferably 75:25 to 90:10. Where the ratio of the fluororesin particles 12 is above the abovementioned range, the hydrophilicity of the antifouling coating 15 can become too low. Furthermore, a large number of hydrophobic portions caused by the fluororesin particles 12 are exposed on the surface, and lipophilic contaminants can easily adhere. Meanwhile, where the ratio of the fluororesin particles 12 is much smaller than the abovementioned range, the hydrophobic portions caused by the fluororesin particles 12 are not sufficiently exposed on the surface of the antifouling coating 15, hydrophilic contaminants can easily adhere, and the desired dust adhesion inhibiting performance sometimes cannot be obtained. The mass of the ultrafine silica particles 11 and the fluororesin particles 12 herein is a value measured by drying the water-based coating composition at 120° C. and removing the moisture.

The thickness of the antifouling composition 15 is not particularly limited but is preferably 0.05 μm or more to 0.5 μm or less. Where the thickness of the antifouling composition 15 is less than 0.05 the desired dust adhesion inhibiting effect sometimes cannot be obtained. Meanwhile where the thickness of the antifouling composition 15 is more than 0.5 μm, defects such as cracks and voids easily appear in the film, depressions and protrusions where the contamination can be easily trapped are formed on the surface, and the desired dust adhesion inhibiting effect sometimes cannot be obtained.

It is preferred that the water-based coating composition include the fluororesin particles 12 as the resin component, but admixing a resin such as included in a coating based on typical resin components is not desirable. One of the features of the antifouling coating 15 in accordance with the present invention is that dust or the like is unlikely to adhere to the porous silica film formed by cohesion of the ultrafine silica particles 11. Therefore, where a resin component such that fills the gaps between the ultrafine silica particles 11 or a resin component such that the ultrafine silica particles 11 are completely covered with the film is present in the water-based coating composition, this feature is lost and a high antifouling effect of the present invention cannot be obtained. The problem that the antifouling effect cannot be obtained does not arise when a particulate resin component which does not cover the ultrafine silica particles 11 entirely with a film is used.

The content of the resin component, or a component that reacts to become a resin component, which can be added to the water-based coating composition is preferably equal to or less than 50% by mass, more preferably equal to or less than 30% by mass of the total amount of the ultrafine silica particles 11, zirconium compound, and fluororesin particles 12 (when such are included). The mass of the ultrafine silica particles 11 and the fluororesin particles 12 in this case is measured by drying the water-based coating composition at 120° C. and removing the moisture. The content of the zirconium compound is calculated on the basis of the mass of zirconium oxide when the entire zirconium in the added zirconium compound becomes zirconium oxide ($ZrO_2$). A water-soluble resin component is included in the content of the abovementioned resin component. Even when the water-soluble resin component is added to the water-based coating composition, this component is easily removed by contact between the antifouling coating 15 and water, thereby ensuring antifouling. Examples of the water-soluble resin component include surfactants, dispersants, and flocculants.

A method for coating the water-based coating composition is not particularly limited, and the coating can be performed using a brush, a sprayer, or a roll coater. In the case of brush or spray coating, when the excess water-based coating composition remaining on the surface is dried, thick portions are locally formed and a problem such as increase of the adhesion of dust at those portions may arise. Therefore, it is preferred that the extra water-based coating composition be removed by allowing the coated solution to stay in order to eliminate the extra water-based coating composition, or by blowing off the extra water-based coating composition with an air blower.

Heating is performed, as necessary, after the antifouling coating 15 has been formed. Where the heating is performed, it is preferred that the coating be allowed to stay in an oven at a temperature from 40° C. or more to 150° C. or less or that hot air at a temperature from 40° C. or more to 150° C. or less be blown. Where the temperature is less than 40° C., the heating effect is not demonstrated. Meanwhile, it is undesirable that the temperature be higher than 150° C., because such a high temperature is highly probable to degrade the hydrophilicity of the antifouling coating 15. The heating time is preferably 15 sec or more to 15 min or less. It is undesirable that the heating time be less than 15 sec, because the temperature of the fin material often does not rise sufficiently. Where the heating time exceeds 15 min, the productivity is lost and the decrease in hydrophilicity is advanced.

Embodiment 2

The antifouling coating according to Embodiment 2 of the present invention has a hydrophilic organic coating as a primary layer for an inorganic coating. Where the antifouling coating of such a form is used in a heat exchanger, good heat exchanger characteristics are obtained. As a result of forming a hydrophilic organic coating as a primary layer on the surface of a heat exchanger, for example, the surface of fins, forming a reaction layer from an aqueous solution comprising a zirconium compound which is at least one selected from zirconium chloride and zirconyl chloride on the hydrophilic organic coating, and forming an inorganic coating from a water-based coating composition comprising ultrafine silica particles on the reaction layer, or forming an inorganic coating from a water-based coating composition comprising ultrafine silica particles and a zirconium compound which is at least one selected from zirconium chloride and zirconyl chloride, it is possible to inhibit the corrosion of fins and maintain the hydrophilicity and antifouling ability for a long time. The hydrophilic organic coating demonstrates an effect of inhibiting the corrosion of the heat exchanger surface. Since the inorganic coating increases the hydrophilicity of the surface, the condensed water is prevented from forming liquid droplets and increasing the ventilation resistance, and the adhesion of dust and fibrous contaminants sucked into the heat exchanger is suppressed.

Figure 3:
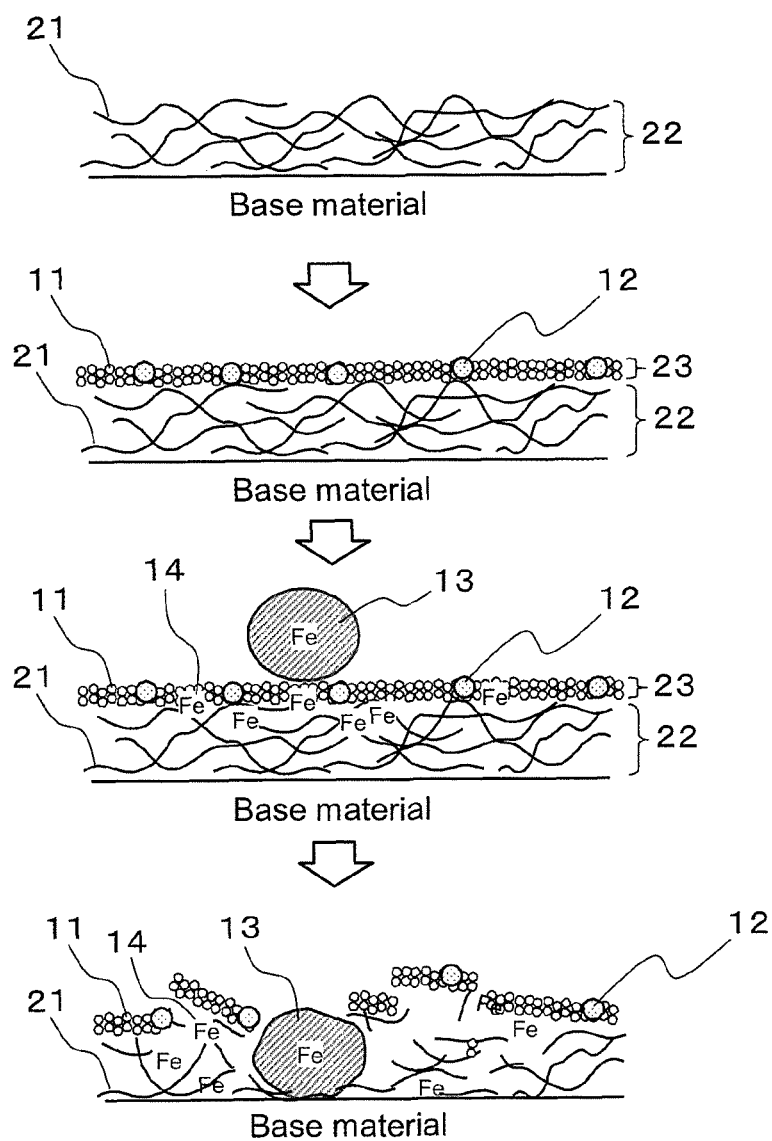
FIG. 3 is a schematic diagram illustrating the degradation of the conventional coating caused by adhesion of metal particles.

FIG. 3 is a schematic diagram illustrating the degradation of the conventional coating caused by adhesion of metal particles. In the conventional coating depicted in FIG. 3, an inorganic coating 23 in which ultrafine silica particles 11 are aggregated and fluororesin particles 12 are distributed in a spot-like fashion is laminated on a hydrophilic organic coating 22 constituted by a polymer 21. With the coating of such a configuration, as has been explained with reference to FIG. 1, dust is unlikely to adhere, but when the coating is wetted with water, the metal particle 13 (for example, an iron particle) adheres thereto. As a result of the metal particle 13 being partially corroded by water, metal ions 14 are released from the metal particle 13. The released metal ions 14 penetrate through the inorganic coating 23 and reach the hydrophilic organic coating 22. The metal ions 14 function as a catalyst and enhance the decomposition of the polymer constituting the hydrophilic organic coating 22. As a result, the hydrophilic organic coating 22 is degraded, the inorganic coating 23 is peeled off, and defects appear in the entire coating. As a result, not only is the metal particle 13 attached to the coating, but where the base material is from a metal, the corrosion thereof is advanced. In such a state, the hydrophilicity and dust adhesion inhibiting effect of the inorganic coating 23 are degraded.

Figure 4:
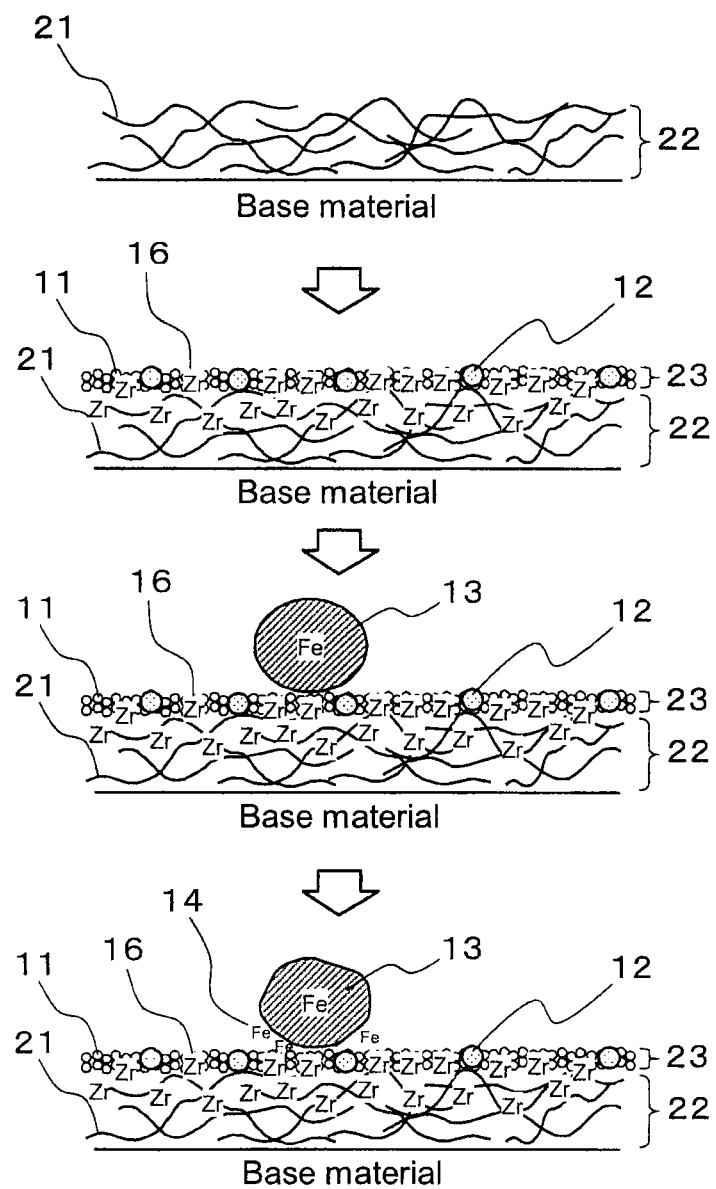
FIG. 4 is a schematic diagram demonstrating that the antifouling coating according to Embodiment 2 of the present invention is unlikely to be degraded by the adhesion of metal particles.

Meanwhile, in the antifouling coating 15 according to Embodiment 2 of the present invention, the effect of the metal particle 13 can be inhibited by using a coating composition comprising a zirconium compound which is at least one selected from zirconium chloride and zirconyl chloride when forming the inorganic coating 23 on the hydrophilic organic coating 22. FIG. 4 is a schematic diagram demonstrating that the antifouling coating 15 according to Embodiment 2 of the present invention is unlikely to be degraded by the adhesion of the metal particle 13. Zirconium chloride or zirconyl chloride act upon the inorganic coating 23 in the same manner as explained in Embodiment 1, but also act to inhibit the effect of the metal particle 13 on the hydrophilic organic coating 22. Thus, zirconium chloride or zirconyl chloride act upon the hydrophilic organic coating 22 when an aqueous solution comprising a zirconium compound which is at least one selected from zirconium chloride and zirconyl chloride is coated on the hydrophilic organic coating 22 and also when a water-based coating composition comprising the ultrafine silica particles, a zirconium compound which is at least one selected from zirconium chloride and zirconyl chloride, and water, which is described in Embodiment 1, is coated on the hydrophilic organic coating 22. The Zr atoms 16 introduced by the zirconium chloride or zirconyl chloride react with the hydroxyl groups in the hydrophilic organic coating 22, crosslink the polymer components, and strengthen the hydrophilic organic coating 22. Such an action can inhibit the effect of the metal particle 13. FIG. 4 illustrates a state in which the hydrophobic fluororesin particles 12 are present in a spot-like fashion in the thin hydrophilic silica film, but the fluororesin particles 12 further inhibit the adhesion of dust, and even when such particles are not present, the effect of inhibiting the attachment of the metal particle 13 can be obtained as a result of adding zirconium chloride or zirconyl chloride. Thus, since the surface of such antifouling coating 15 in such heat exchanger is constituted by a continuous hydrophilic portion in which hydrophobic portions are present, when water droplets adhere thereto, the droplets are easily spread and the film, when viewed as a whole, demonstrates high hydrophilicity. Further, because of a configuration in which hydrophilic portions and hydrophobic portions are finely mixed, even when hydrophilic dust such as sand dust or hydrophobic dust, such as soot, flies together with the air flow and attempts to adhere to the heat exchanger surface, the dust comes into contact with the surface having opposite nature and cannot stably adhere to the surface. Thus, strong antifouling ability is demonstrated with respect to a wide range of dust-like contaminants.

The hydrophilic organic coating 22 of Embodiment 2 may be a film that includes a polymer having a polar group and that is not soluble in water. The type of the polymer is not particularly limited, and examples of suitable polymers include polyvinyl alcohol, polyvinyl pyrrolidone, and polyacrylamide homopolymers, copolymers and modification products thereof, acrylic acid and methacrylic acid homopolymers, copolymers and salts thereof, and various epoxy resins and urethane resins. Those compounds may be used individually or as mixtures of different types thereof. Further, among fluororesins and silicones, those having polar groups can be used. Further, a composition in which polymers of a large number of types are mixed homogeneously or exist as separate phases, have a particulate shape, or are mixed with a component functioning as a binder therefor may be also used.

A crosslinking agent, a radical initiator, a reactive component, and inorganic particles such as silica and titania may be also added to the coating composition for forming the hydrophilic organic coating 22 in order to make it insoluble or increase the strength thereof.

The thickness of the hydrophilic organic coating 22 is preferably from 0.1 μm or more to 15 μm or less. Where the thickness of the hydrophilic organic coating 22 is less than 0.1 μm, the coating will be too thin, and sufficient anticorrosive effect sometimes cannot be obtained. Meanwhile, it is also undesirable that the thickness of the hydrophilic organic coating 22 exceed 15 μm, because the film becomes too thick and the efficiency of heat transfer decreases.

The reaction of zirconium chloride or zirconyl chloride may be performed with respect to the hydrophilic organic coating 22, the inorganic coating 23, or both coatings.

Where the zirconium chloride or zirconyl chloride is caused to act directly on the hydrophilic organic coating 22, an aqueous solution comprising zirconium chloride or zirconyl chloride may be coated on the hydrophilic organic coating 22. With this method, a reaction layer is formed by reacting the zirconium chloride or zirconyl chloride at a sufficiently high density with the hydrophilic organic coating 22, instead of relying on a complex process. The advantage of such a reaction layer is that metal ions 14 released from the metal particle 13 can be more effectively prevented from penetrating into the hydrophilic organic coating 22. Furthermore, as explained in Embodiment 1, the concentration of zirconium chloride or zirconyl chloride in the water-based coating composition comprising ultrafine silica particles 11, a zirconium compound which is at least one selected from zirconium chloride and zirconyl chloride, and water has a low value equal to or less than 50% by mass of the solid weight of the ultrafine silica particles, but with the method of coating an aqueous solution comprising zirconium chloride or zirconyl chloride, a higher concentration can be obtained. Therefore, zirconium chloride or zirconyl chloride can be reacted with the hydrophilic organic coating 22 to obtain a higher density. In the aqueous solution to be used in the case of a direct reaction with the hydrophilic organic coating 22, a zirconium compound which is at least one selected from zirconium chloride and zirconyl chloride is contained preferably at 0.1% by mass or more to 40% by mass or less, more preferably at 0.2% by mass or more to 15% by mass or less. Where the content of the zirconium compound is less than 0.1% by mass, the number of Zr atoms 16 introduced into the hydrophilic organic coating 22 is too small and a sufficient effect sometimes cannot be obtained. Meanwhile, where the content of the zirconium compound exceeds 40% by mass, excess compound adheres to the surface and they can adversely affect the formation of the inorganic coating 23. The content of the zirconium compound, as referred to herein, is calculated on the basis of the mass of zirconium oxide when the entire zirconium in the added zirconium compound becomes zirconium oxide ($ZrO_2$).

A method for coating the abovementioned aqueous solution is not particularly limited and the coating may be performed by using a sprayer or a roller, or by dipping or casting. The coating can be dried by natural drying at a normal temperature, but the reaction can be accelerated and a stronger hydrophilic organic coating 22 can be obtained by performing the drying with hot air or by heating in an oven. The heating temperature in this case is preferably from 40° C. or more to 250° C. or less. Where the heating temperature is less than 40, the drying is not performed rapidly. It is also undesirable that the heating temperature exceed 250° C. because the hydrophilic organic coating 22 can be thermally degraded and cracks can appear therein. The merit of the heating treatment performed at this time is that where the inorganic coating 23 is treated, the treatment can be performed at a temperature at which a problem such as decrease in hydrophilicity arises.

Further, as a result of forming the inorganic coating 23 on the reaction layer by coating a water-based coating composition comprising the ultrafine silica particles 11, an antifouling coating 15 is obtained which is constituted of the hydrophilic organic coating 22, the reaction layer, and the inorganic coating 23. The type and content of the ultrafine silica particles 11 used in this case are the same as in Embodiment 1. Further, the fluororesin particles 12 may be also introduced into the water-based coating composition used herein, and the type and content thereof are the same as in Embodiment 1.

A method for coating the water-based coating composition is not particularly limited, and the coating can be performed using a brush, a sprayer, or a roll coater. In the case of brush or spray coating, when the excess water-based coating composition remaining on the surface is dried, thick portions are locally formed and a problem such as increase of the adhesion of dust at those portions may arise. Therefore, it is preferred that the extra water-based coating composition be removed by allowing the coated solution to stay in order to eliminate the extra water-based coating composition, or by blowing off the extra water-based coating composition with an air blower.

Heating is performed, as necessary, after the inorganic coating 23 has been formed. When said heating is performed, it is preferred that the coating be allowed to stay in an oven at a temperature from 40° C. or more to 150° C. or less or have hot air blowing on it at a temperature from 40° C. or more to 150° C. or less. Where the temperature is less than 40° C., there will be no heating effect. Meanwhile, it is also undesirable that the temperature be higher than 150° C., because it is highly probable that such a high temperature will degrade the hydrophilicity of the inorganic coating 23. The heating time is preferably 15 sec or more to 15 min or less. It is undesirable that the heating time be less than 15 sec, because the temperature of the fin material often does not rise sufficiently. Where the heating time exceeds 15 min, productivity is lost and the decrease in hydrophilicity is advanced.

Meanwhile, in order to cause the zirconium chloride or zirconyl chloride to act upon the hydrophilic organic coating 22 and the inorganic coating 23, a method can be used by which the hydrophilic organic coating 22 and the inorganic coating 23 are formed and then treated with an aqueous solution comprising a zirconium compound which is at least one selected from zirconium chloride and zirconyl chloride. A method that involves simpler steps than the above-described method includes coating a water-based coating composition comprising the ultrafine silica particles 11, a zirconium compound which is at least one selected from zirconium chloride and zirconyl chloride, and water on the hydrophilic organic coating 22, this method being described in Embodiment 1. With this method, the step of coating an aqueous solution including a zirconium compound which is at least one selected from zirconium chloride and zirconyl chloride can be omitted, and the adhesion of the hydrophilic organic coating 22 and the inorganic coating 23 can be increased.

A method by which the contact time of the water based coating composition and the hydrophilic organic coating 22 prior to drying is extended, for example, a method by which the time of dipping into the water-based coating composition or the time of spraying the water-based coating composition with a sprayer is extended, can be used to increase the reliability of the reaction of zirconium chloride or zirconyl chloride. With this method, the reaction can be sufficiently enhanced by setting the contact time to 10 sec or longer, preferably to about 30 sec. Where the contact time is less than 10 sec, no difference with the usual coating can be found. It is also undesirable that the contact time be in excess of 30 sec because practically no additional effect is produced. Increasing the temperature of the water-based coating composition or coating object is another method for making the reaction of zirconium chloride or zirconyl chloride more reliable. The reaction is easily accelerated by setting this temperature from 30° C. or more to 60° C. or less. Where the temperature is less than 30° C., the heating effect is too small. It is also undesirable that the temperature be higher than 60° C. because the evaporation of the water-based coating composition is intensified and drying is accelerated, yet conversely, the reaction with the hydrophilic organic coating 22 is accordingly decelerated and thus a homogeneous coating is difficult to obtain.

Where the above-described antifouling coating 15 is formed on the heat exchanger fins, it is preferred that the coating composition be applied to the fins after the pipe in which the coolant flows has been joined to the fins and the heat exchanger has been assembled. Where the heat exchanger is assembled after forming the antifouling coating 15 on the fins, since the fin material is subjected to such operations as punching, pressing, and pipe insertion, the antifouling coating 15 can be damaged. This can be avoided by applying the coating composition to the fins after the pipe in which the coolant flows has been joined to the fins and the heat exchanger be assembled. The coating in this case can be performed by spraying or dipping. It is also preferred that excess liquid be removed by allowing the coating composition or aqueous solution to stay after the coating application to eliminate the excess liquid, or by shaking off the excess liquid by moving, for example, rotating, the heat exchanger, or by blowing the extra liquid off with an air blower. It is also preferred that only the formation of the hydrophilic organic coating 22 be performed on the unassembled fin materials and that the aqueous solution or water-based coating composition be coated after the heat exchanger has been assembled.

EXAMPLES

The present invention will be explained in detail below with reference to examples, but the present invention is not limited to these examples.

Example 1

A water-based coating composition having the composition shown in Table 1 was prepared by stirring and mixing pure water, colloidal silica (Snowtex OXS manufactured by Nissan Kagaku Kogyo KK) comprising ultrafine silica particles with an average particle size of 6 nm, a PTFE dispersion with an average particle size of 150 nm, and zirconium chloride (12% by mass of the ultrafine silica particles), adding a nonionic surfactant (polyoxyethylene lauryl alkyl ester) at 0.1% by mass to the mixture, and further stirring and mixing.

The obtained water-based coating composition was coated on an aluminum fin material and dried with an air blower. The aluminum fin material with the coating formed thereon was wetted by dipping it into water, an iron powder with an average particle size of 45 μm was blown thereon, followed by drying with an air blower, and the adhesion state of the iron powder was observed. The adhesion state of the iron powder was visually evaluated. The evaluation used 6 grades. When the iron powder adhesion was induced to the untreated aluminum fin (Comparative Example 4), a large amount of iron powdered has adhered, and this state was evaluated by grade 5, the state in which absolutely no iron powder has adhered was evaluated by grade 0.

The aluminum fin material with the iron powder adhered thereto was allowed to stay for 3 days at a humidity of 90% and then sprayed with water. The contamination state thereof was then visually checked.

The contact angle was measured with a contact angle meter PD-X (Kyowa Kaimen Kagaku).

The results are shown in Table 2.

Example 2

A water-based coating composition having the composition shown in Table 1 was prepared by stirring and mixing pure water, colloidal silica (Snowtex OXS manufactured by Nissan Kagaku Kogyo KK) comprising ultrafine silica particles with an average particle size of 6 nm, a PTFE dispersion with an average particle size of 150 nm, and zirconium chloride (10% by mass of the ultrafine silica particles), adding a nonionic surfactant (polyoxyethylene lauryl alkyl ester) at 0.1% by mass to the mixture, and further stirring and mixing. An aluminum fin material with a coating formed thereon was fabricated in the same manner as in Example 1, except that this water-based coating composition was used. The evaluation was performed in the same manner as in Example 1. The results are shown in Table 2.

Example 3

An aluminum fin material with a coating formed thereon was fabricated in the same manner as in Example 1, except that zirconyl chloride was used instead of zirconium chloride. The evaluation was performed in the same manner as in Example 1. The results are shown in Table 2.

Example 4

An aluminum fin material with a coating formed thereon was fabricated in the same manner as in Example 2, except that zirconyl chloride was used instead of zirconium chloride. The evaluation was performed in the same manner as in Example 1. The results are shown in Table 2.

Example 5

An aluminum fin material with a coating formed thereon was fabricated in the same manner as in Example 1, except that the PTFE dispersion was not used. The evaluation was performed in the same manner as in Example 1.

The results are shown in Table 2.

Comparative Example 1

An aluminum fin material with a coating formed thereon was fabricated in the same manner as in Example 1, except that the content of zirconium chloride was changed to 60% by mass of the ultrafine silica particles. The evaluation was performed in the same manner as in Example 1. The results are shown in Table 2.

Comparative Example 2

An aluminum fin material with a coating formed thereon was fabricated in the same manner as in Example 1, except that zirconium chloride was not used. The evaluation was performed in the same manner as in Example 1. The results are shown in Table 2.

Comparative Example 3

An aluminum fin material with a coating formed thereon was fabricated in the same manner as in Example 1, except that the PTFE dispersion and zirconium chloride were not used. The evaluation was performed in the same manner as in Example 1. The results are shown in Table 2.

Comparative Example 4

The untreated aluminum fin material (the aluminum fin material on which the coating has not been formed) was evaluated in the same manner as in Example 1. The results are shown in Table 2.

TABLE 1

|  | Ultrafine silica particles (% by mass) | Fluororesin particles (% by mass) | Zirconium compound (% by mass) |
|---|---|---|---|
| Example 1 | 2.5 | 0.5 | 0.3 (zirconium chloride) |
| Example 2 | 3.0 | 1.0 | 0.3 (zirconium chloride) |
| Example 3 | 2.5 | 0.5 | 0.3 (zirconyl chloride) |
| Example 4 | 3.0 | 1.0 | 0.5 (zirconyl chloride) |
| Example 5 | 2.5 | None | 0.3 (zirconium chloride) |
| Comparative Example 1 | 2.5 | 0.5 | 1.5 (zirconium chloride) |
| Comparative Example 2 | 2.5 | 0.5 | None |
| Comparative Example 3 | 2.5 | None | None |
| Comparative Example 4 | None | None | None |

TABLE 2

|  | Contact angle | State after wet adhesion of iron powder and drying | Attachment state of iron powder after stationary period and washing with water |
|---|---|---|---|
| Example 1 | 11° | 1 | Iron powder slightly attached |
| Example 2 | 12° | 2 | Iron powder slightly attached |
| Example 3 | 11° | 2 | Iron powder not attached |
| Example 4 | 12° | 1 | Iron powder slightly attached |
| Example 5 | 11° | 3 | Iron powder not attached |
| Comparative Example 1 | 25° | 4 | Iron powder not attached |
| Comparative Example 2 | 11° | 2 | Iron powder attached |
| Comparative Example 3 | 12° | 4 | Iron powder attached |
| Comparative Example 4 | 45° | 5 | Iron powder attached |

The results shown in Table 2 that relate to the adhesion of iron powder demonstrate that the adhesion to the aluminum fin material coated with the ultrafine silica film (Comparative Example 3) decreased with respect to that to the untreated aluminum fin material of Comparative Example 4, and the adhesion to the aluminum fin material coated with the ultrafine silica film and fluororesin particles (Comparative Example 2) decreased further. With the coating comprising excess zirconium chloride (Comparative Example 1), the iron powder adhesion inhibition effect decreased. The hydrophilicity was increased by the coating in all examples, except for Comparative Example 1 with excess zirconium chloride in which the hydrophilicity decreased.

High hydrophilicity was obtained in all of Examples 1 to 5, and the adhesion of iron powder in those examples was small. In Example 5, the adhesion of iron powder was slightly larger than in Examples 1 to 4, which is due to the fact that the fluororesin particles were not added. Further, in Example 5, the adhesion of iron powder was less than in Comparative Example 3. This result indicates that the addition of zirconium chloride inhibits the adhesion of iron powder.

When the iron powder was corroded, in Comparative Examples 2 to 4 in which no zirconium compound was added, the rust strongly attached to the surface and was not stripped with the sprayer, whereas in Examples 1 to 5 and Comparative Example 1, the rust attachment was significantly inhibited. Further, in Examples 1 to 5, high hydrophilicity and dust adhesion inhibiting effect were obtained and it was difficult for the adhered iron powder to attach even after being corroded.

Examples 6 and 7

An aqueous solution in which 3% by mass of polyvinyl alcohol Z-200 (Nippon Gosei Kagaku KK) was mixed with 5% by mass, on the basis of the polyvinyl alcohol, of glyoxazole was coated on an aluminum fin material, and heated for 5 min at 150° C. to form a hydrophilic organic coating with a thickness of 0.7 µm. An aqueous solution comprising 5% by mass of zirconyl chloride was coated on the hydrophilic organic coating and dried with an air blower at a normal temperature to form a reaction layer (pretreatment). Then, a water-based coating composition comprising the components presented in Table 3 was coated on the reaction layer and dried with an air blower to form an inorganic coating.

The aluminum fin material after the formation of the coating was wetted by dipping it into water, an iron powder with an average particle size of 45 µm was blown thereon, drying was performed with an air blower, and the adhesion state of the iron powder was observed. The adhesion state of the iron powder was determined visually. The evaluation used 6 grades. When only the hydrophilic organic coating was present (Comparative Example 5), a black stained state was observed and this state was evaluated as grade 5, and the state in which absolutely no iron powder adhered was evaluated as grade 0.

The coating was allowed to stay for 3 days at a humidity of 90% in a state with adhered iron powder, water was then sprayed with a sprayer, and the state of the corroded iron powder was checked. Changes in the coating close to the iron particles were checked by immersing the coating for 1 min into a 1% aqueous solution of sodium hydroxide. The results are shown in Table 4.

Examples 8 and 9

An aqueous solution in which 3% by mass of polyvinyl alcohol Z-200 (Nippon Gosei Kagaku KK) was mixed with 5% by mass, on the basis of the polyvinyl alcohol, of glyoxazole was coated on an aluminum fin material, and heated for 5 min at 150° C. to form a hydrophilic organic coating with a thickness of 0.7 µm. A water-based coating composition comprising the components presented in Table 3 was coated on a reaction layer and dried with an air blower to form an inorganic coating on the hydrophilic organic coating, thereby producing an aluminum fin material with a coating formed thereon. The evaluation was performed in the same manner as in Examples 6 and 7. The results are shown in Table 4.

Comparative Example 5

An aqueous solution in which 3% by mass of polyvinyl alcohol Z-200 (Nippon Gosei Kagaku KK) was mixed with 5% by mass, on the basis of the polyvinyl alcohol, of glyoxazole was coated on an aluminum fin material, and heated for 5 min at 150° C. to form a hydrophilic organic coating with a thickness of 0.7 µm, thereby producing an aluminum fin material with a coating formed thereon. The evaluation was performed in the same manner as in Examples 6 and 7. The results are shown in Table 4.

Comparative Examples 6 and 7

An aqueous solution in which 3% by mass of polyvinyl alcohol Z-200 (Nippon Gosei Kagaku KK) was mixed with 5% by mass, on the basis of the polyvinyl alcohol, of glyoxazole was coated on an aluminum fin material, and heated for 5 min at 150° C. to form a hydrophilic organic coating with a thickness of 0.7 µm. A water-based coating composition comprising the components presented in Table 3 was coated on a reaction layer and dried with an air blower to form an inorganic coating on the hydrophilic organic coating, thereby producing an aluminum fin material with a coating formed thereon. The evaluation was performed in the same manner as in Examples 6 and 7. The results are shown in Table 4.

TABLE 3

|  | Ultrafine silica particles (% by mass) | Fluororesin particles (% by mass) | Zirconyl chloride (% by mass) |
|---|---|---|---|
| Example 6 | 1.5 | None | Pretreatment |
| Example 7 | 1.5 | 0.3 | Pretreatment |
| Example 8 | 1.5 | None | 0.3 |
| Example 9 | 1.5 | 0.3 | 0.5 |
| Comparative Example 5 | — | — | — |
| Comparative Example 6 | 1.5 | None | None |
| Comparative Example 7 | 1.5 | 0.3 | None |

TABLE 4

|  | Contact angle | State after wet adhesion of iron powder and drying | Attachment state of iron powder after stationary period and washing with water | Film state of iron powder adhesion portion after washing with alkali |
|---|---|---|---|---|
| Example 6 | 9° | 2 | Iron powder not attached, no coloration | No peeling |
| Example 7 | 10° | 1 | Iron powder slightly attached, no coloration | No peeling |
| Example 8 | 12° | 2 | Iron powder not attached, slight coloration | No peeling |
| Example 9 | 12° | 1 | Iron powder not attached, slight coloration | No peeling |
| Comparative Example 5 | 45° | 5 | Iron powder attached, coloration | Peeling |
| Comparative Example 6 | 11° | 1 | Iron powder attached, coloration | Peeling |
| Comparative Example 7 | 10° | 2 | Iron powder attached, coloration | Partial peeling |

The hydrophilicity was determined from the contact angle, the antifouling performance is determined from the state of the iron powder after wet adhesion and drying, the iron rust attachment state and coloration caused by iron ions are determined from the attachment state of the iron powder after washing with water, and the degree of degradation of the hydrophilic organic coating caused by iron ions is determined from the state of the coating in the iron powder adhesion portions after washing with an alkali.

According to the results in Table 4, in Comparative Example 5, the contact angle in a dry state is 45° and the hydrophilicity is low. In Comparative Example 5, hydrophilicity increases in the humidified state and the coating becomes hydrophilic. In Comparative Example 5, the iron powder easily adhered and the antifouling ability is low. In Comparative Example 5, when the coating is stored in a humidified state, iron rust is attached thereto and the coating is discolored into a brown-black color. This result indicates that the attachment of dust comprising the iron powder, or the like, easily occurs. Further, in alkali washing, the coating has dissolved and peeled off in the iron powder adhesion portions. It follows from this result that the film has been degraded by the produced iron ions.

In Comparative Examples 6 and 7, the hydrophilic organic coating is covered by the inorganic coating. The contact angle indicates that the hydrophilicity is high, and the iron powder adhesion state indicates that the antifouling ability is also high. However, where the coating is stored in a humidified state, iron rust is easily attached, and the hydrophilic organic coating is degraded and peeled off.

In Examples 6 and 7, the hydrophilicity is high and the antifouling performance is also high. Even when the iron powder is corroded, the level of attachment and coloration is low. Furthermore, the hydrophilic organic coating is not peeled off by an alkali and the effect of iron ions is inhibited. In particular, the coloration of the hydrophilic organic coating is significantly suppressed, and the polymer components are apparently efficiently protected by direct treatment of the hydrophilic organic coating. The comparison of Example 6 and Example 7 demonstrates that Example 7 is superior in the antifouling performance, and the effect of the addition of fluororesin particles is demonstrated.

In Examples 8 and 9, the hydrophilicity is high and the antifouling performance is also high. Even when the iron powder is corroded, the level of attachment and coloration is low. Furthermore, the hydrophilic organic coating is not peeled off by an alkali and the effect of iron ions is inhibited. In particular, the attachment of iron rust is significantly suppressed, and the inorganic coating is apparently efficiently protected due to the addition of zirconium chloride to the inorganic coating. The comparison of Example 8 and Example 9 demonstrates that Example 9 is superior in the antifouling performance, and the effect of the addition of fluororesin particles is demonstrated.

EXPLANATION ON NUMERALS

11—ultrafine silica particles; 12—fluororesin particles; 13—metal particle; 14—metal ions; 15—antifouling coating; 16—Zr atoms; 21—polymer; 22—hydrophilic organic coating; 23—inorganic coating.

The invention claimed is:
1. A method for manufacturing a heat exchanger, comprising: joining a fin with a hydrophilic organic coating formed thereon to a pipe in which a coolant flows; and forming, on the hydrophilic organic coating, a reaction layer from an aqueous solution comprising a zirconium compound which is at least one selected from zirconium chloride and zirconyl chloride and then forming, on the reaction layer, an inorganic coating from a water-based coating composition comprising 0.1% by mass to 10% by mass of ultrafine silica particles having an average particle size equal to or less than 25 nm.

2. A method for manufacturing a heat exchanger according to claim 1, wherein the water-based coating composition further comprises fluororesin particles having an average particle size from 50 nm to 500 nm.

3. A heat exchanger comprising a pipe in which a coolant flows, and a fin attached to the pipe, the heat exchanger comprising:

(a) a hydrophilic organic coating formed on the fin; a reaction layer obtained by reacting a zirconium compound which is at least one selected from zirconium chloride and zirconyl chloride on a surface layer of the hydrophilic organic coating; and an inorganic coating provided on the reaction layer and formed from a water-based coating composition comprising 0.1% by mass to 10% by mass of ultrafine silica particles having an average particle size equal to or less than 25 nm.

4. The method of claim 1, wherein the water-based coating composition comprises 0.2% by mass to 10% by mass of ultrafine silica particles having an average particle size equal to or less than 25 nm.

5. The method of claim 1, wherein the water-based coating composition comprises 0.2% by mass to 4% by mass of ultrafine silica particles having an average particle size equal to or less than 25 nm.

6. The method of claim 1, wherein the zirconium compound is zirconium chloride and zirconyl chloride.

7. The method of claim 1, wherein the zirconium compound is zirconium chloride.

8. The method of claim 1, wherein the zirconium compound is zirconyl chloride.

9. The heat exchanger of claim 3, wherein the water-based coating composition comprises 0.2% by mass to 10% by mass of ultrafine silica particles having an average particle size equal to or less than 25 nm.

10. The heat exchanger of claim 3, wherein the water-based coating composition comprises 0.2% by mass to 4% by mass of ultrafine silica particles having an average particle size equal to or less than 25 nm.

11. The heat exchanger of claim 3, wherein the zirconium compound is zirconium chloride and zirconyl chloride.

12. The heat exchanger of claim 3, wherein the zirconium compound is zirconium chloride.

13. The heat exchanger of claim 3, wherein the zirconium compound is zirconyl chloride.

* * * * *